United States Patent
Schweers et al.

(10) Patent No.: US 6,362,305 B1
(45) Date of Patent: Mar. 26, 2002

(54) METHOD FOR PRODUCING FORMALDEHYDE FROM METHANOL

(75) Inventors: Elke Schweers, Bad Soden; Thomas Kaiser, Kelkheim; Christine Meister, Sulzbach; Michael Rosenberg, Niedernhausen; Rolf Schulz, Dinslaken, all of (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/445,083

(22) PCT Filed: May 26, 1998

(86) PCT No.: PCT/EP98/03084

§ 371 Date: Feb. 28, 2000

§ 102(e) Date: Feb. 28, 2000

(87) PCT Pub. No.: WO98/55436

PCT Pub. Date: Dec. 10, 1998

(30) Foreign Application Priority Data

Mar. 31, 1998 (DE) .......................... 198 14 285

(51) Int. Cl.$^7$ .......................... C08G 10/00; C07C 47/00

(52) U.S. Cl. .......................... 528/230; 526/64; 526/66; 526/67; 526/68; 526/71; 528/232; 528/246; 528/392; 568/420; 568/422; 568/429

(58) Field of Search .......................... 526/64, 66, 67, 526/68, 71; 528/230, 232, 246, 392; 568/420, 422, 429

(56) References Cited

U.S. PATENT DOCUMENTS 4,014,939 A * 3/1977 Osugi et al.

FOREIGN PATENT DOCUMENTS

GB 1505396 * 3/1978

* cited by examiner

*Primary Examiner*—Samuel A. Acquah
(74) *Attorney, Agent, or Firm*—Connolly Bove Lodge & Hutz LLP

(57) ABSTRACT

In a process for preparing formaldehyde from methanol by dehydrogenation in a reactor in the presence of a catalyst at a temperature in the range from 300 to 1000° C., a circulating gas stream comprising by-products of the dehydrogenation is passed through the reactor.

14 Claims, 3 Drawing Sheets

METHOD FOR PRODUCING FORMALDEHYDE FROM METHANOL

Figure 1:
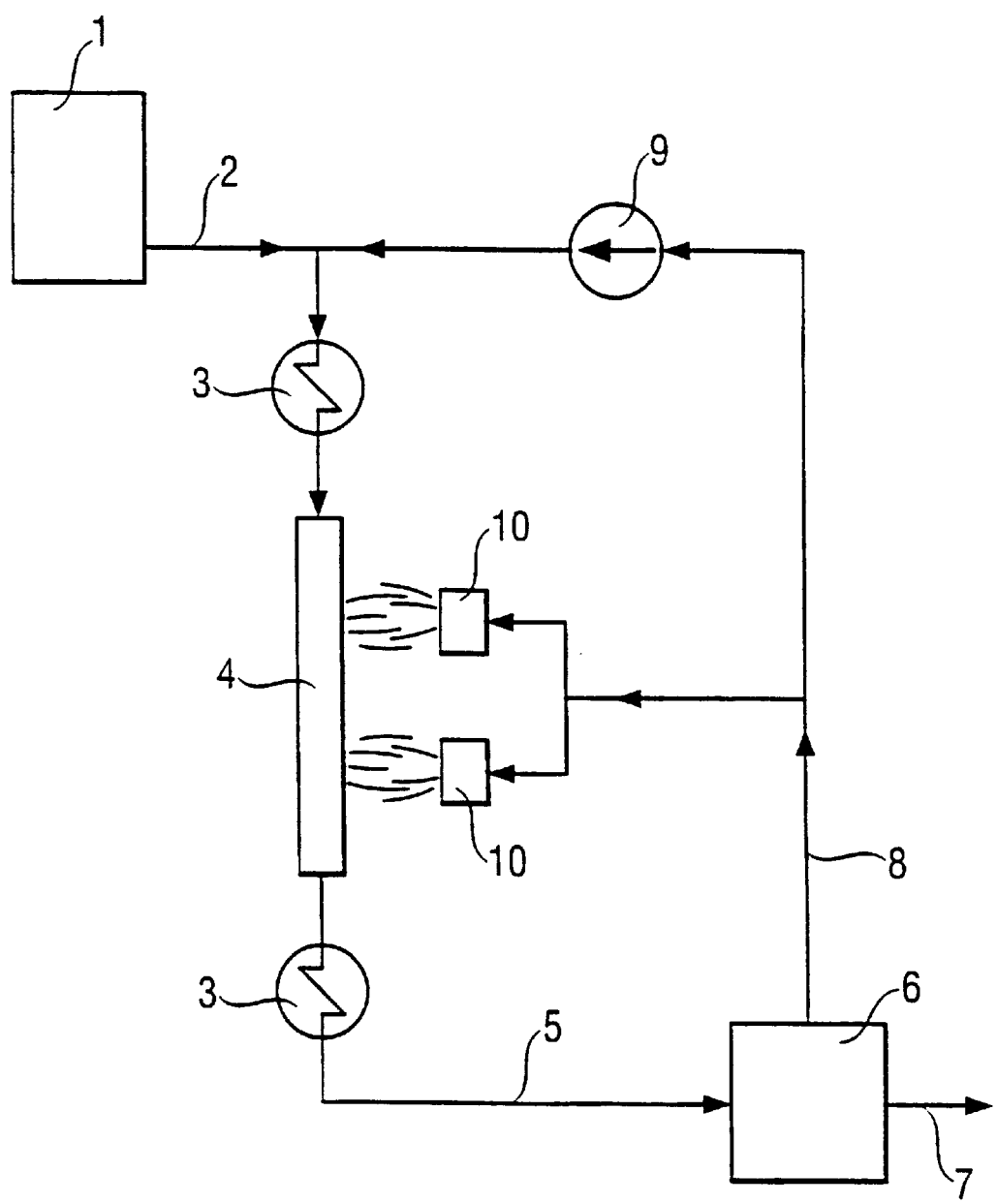

A number of processes for preparing formaldehyde from methanol are known (see, for example, Ullmann's Encyclopaedia of Industrial Chemistry). The processes carried out industrially are predominantly the oxidation:

$$CH_3OH + \tfrac{1}{2}O_2 \rightarrow CH_2O + H_2O$$

over catalysts comprising iron oxide and molybdenum oxide at from 300° C. to 450° C. (Formox process) and the oxidative dehydrogenation (silver catalyst process) according to:

$$CH_3OH \rightarrow CH_2O + H_2$$

$$H_2 + \tfrac{1}{2}O_2 \rightarrow H_2O$$

at from 600° C. to 720° C. In both processes, the formaldehyde is first obtained as an aqueous solution. Particularly when used for the preparation of formaldehyde polymers and oligomers, the resulting formaldehyde has to be subjected to costly dewatering. A further disadvantage is the formation, as by-product, of the corrosive formic acid which has an adverse effect on the polymerization.

The dehydrogenation of methanol enables these disadvantages to be avoided and, in contrast to the abovementioned processes, virtually water-free formaldehyde to be obtained directly:

$$CH_3OH \xrightarrow{\text{cat.}} CH_2O + H_2$$

In order to achieve an ecologically and economically interesting industrial process for the dehydrogenation of methanol, the following prerequisites have to be met: The strongly endothermic reaction has to be carried out at high temperatures so as to be able to achieve high conversions. Competing secondary reactions have to be suppressed in order to achieve satisfactory selectivity to formaldehyde (without catalysis, the selectivity for forming formaldehyde is less than 10% at conversions over 90%). The residence times have to be short and the cooling of the reaction products has to be rapid in order to lessen the decomposition of the formaldehyde which is not thermodynamically stable under the reaction conditions:

$$CH_2O \rightarrow CO + H_2$$

Various methods of carrying out this reaction have been proposed; thus, for example, DE-A-37 19 055 describes a process for preparing formaldehyde from methanol by dehydrogenation in the presence of a catalyst at elevated temperature. The reaction is carried out in the presence of a catalyst comprising at least one sodium compound at a temperature of from 300° C. to 800° C.

J. Sauer and G. Emig (Chem. Eng. Technol. 1995, 18, 284–291) were able to set free a catalytically active species, presumed by them to be sodium, from a catalyst comprising $NaAlO_2$ and $LiAlO_2$ by means of a reducing gas mixture ($87\%N_2 + 13\%H_2$). This species can catalyze the dehydrogenation of methanol added downstream in the same reactor, i.e. methanol which does not come into contact with the catalyst bed, to give formaldehyde. When using nonreducing gases, only a low catalytic activity was observed.

According to J. Sauer and G. Emig and also results from more recent studies (see, for example, M. Bender et al., Presentation to the XXX. Jahrestreffen deutscher Katalytiker, Mar. 21–23, 1997), sodium atoms and NaO molecules have been identified as species emitted into the gas phase and their catalytic activity for the dehydrogenation of methanol in the gas phase has been described.

In the known processes, the starting material methanol is always reacted diluted with nitrogen and/or nitrogen/hydrogen mixtures.

Although good results are already achieved using the known processes, there is still a wide scope for improvements from a technical and economic point of view.

In various documents, for example EP-A 0 130 068, EP-A 0 261 867 and DE-A 25 25 174, it is proposed that the gas mixture formed in the reaction be used as fuel after separating off the formaldehyde.

It has now surprisingly been found that a reaction procedure which is greatly improved from a technical and economic point of view, particularly in terms of energy, can be achieved if the gas mixture formed in addition to the formaldehyde is used for diluting the starting material methanol.

The invention accordingly provides a process for preparing formaldehyde from methanol by dehydrogenation in a reactor in the presence of a catalyst at a temperature in the range from 300 to 1000° C., wherein a circulating gas stream comprising by-products of the dehydrogenation is passed through the reactor.

The process of the invention is an ecologically and economically favorable method of producing formaldehyde having a low water content. The utilization of the hydrogen-rich by-products of the reaction, i.e. the product gas after separating off the formaldehyde, for diluting the starting material methanol for the dehydrogenation enables, on the one hand, particularly high yields to be achieved and, on the other hand, owing to the good thermal conductivity, allows the outlay in terms of apparatus for heating the starting materials, introducing the heat of reaction and cooling the products to be minimized. The further possible utilization of parts of the by-products of the reaction, i.e. the product gas after separating off the formaldehyde, as fuel for generating the reaction temperature necessary for the dehydrogenation, and also heat recovery from the waste gases, can provide the heat for this and further process steps. In this case, essentially only the desired product formaldehyde and the combustion products $CO_2$ and $H_2O$ leave the process.

For the purposes of the invention, dehydrogenation is a non-oxidative process according to the equation:

$$CH_3OH \xrightarrow{\text{cat.}} CH_2O + H_2$$

For the purposes of the invention, the term "by-products" refers to the gas mixture which remains after separating off the product formaldehyde and comprises, apart from hydrogen, usually CO, $CH_4$ and $CO_2$ as well as possibly $CH_2O$, MeOH, $H_2O$, $HCOOCH_3$ and/or residues from the separating off of formaldehyde, and preferably consists essentially of these gases. The ratio $H_2/CO$ in the circulating gas is particularly preferably $\geq 3$.

FIG. 1 shows a schematic overview of a preferred variant of the process of the invention.

Methanol 2 is taken from a reservoir 1, diluted with circulating gag 8, preheated in a heat exchanger 3 and introduced into the reactor 4. After going through the reactor 4, the gas is cooled in a heat exchanger 3' and the product mixture 5 is separated in the separation vessel 6 into formaldehyde 7 and by-products 8 (circulating gas). At least part of the by-products is recirculated to the reactor by means of a conveying device 9, for example a fan. A part of the by-products can after discharge be used directly as fuel in an apparatus 10 for firing the reaction vessel 4. The heat exchangers 3, 3' can be a single unit.

The invention further provides an apparatus for carrying out the abovementioned process comprising a heat exchanger for preheating the starting materials, a reactor for carrying out the dehydrogenation, a heat exchanger for cooling the product mixture, a separation vessel for separating off the formaldehyde and also means, in particular a fan, for recirculating at least part of the by-products of the reaction to the reactor.

In a preferred embodiment of the apparatus of the invention, the apparatus further comprises means for discharging a further part of the by-products of the dehydrogenation and for feeding this part to an apparatus for heating the reactor in which latter apparatus it serves as fuel.

Commercial methanol can be used for the reaction; it should preferably be low in water and contain no substances which poison the catalyst.

To carry out the dehydrogenation, the fluid, preferably gaseous, methanol is diluted with gaseous by-products of the dehydrogenation.

The molar proportion of methanol is generally from 5 to 90%, preferably from 10 to 50%, particularly preferably from 10 to 40%. The amount of circulating gas required follows from the proportion of methanol.

The pressure is not critical in the process of the invention. The dehydrogenation of the methanol can be carried out at subatmospheric pressure, atmospheric pressure or superatmospheric pressure. A range of from about 0.1 to 10 bar, preferably from 0.5 to 2 bar, is particularly useful. Preference is given to atmospheric pressure. The process of the invention can be carried out batchwise or continuously, with preference being given to the latter. The temperature is generally from 300° C. to 950° C., preferably from 500 to 900° C., particularly preferably from 600 to 850° C.

Preferably from 0.01 to 1 kg of methanol per hour and per gram of catalyst used is reacted. In the case of a continuous process, further catalyst has to be introduced continuously or discontinuously. The amounts involved here are generally from 10 milligrams to 5 grams, preferably from 10 mg to 1 g, particularly preferably from 50 to 1000 mg, very particularly preferably from 50 to 500 mg, per kg of methanol reacted.

The catalysts used can be, for example, those known from the literature, as are described, for example, in Chem. Eng. Technol. 1994, 17, 34.

Suitable metals are, for example, Li, Na, K, Cs, Mg, Al, In, Ga, Ag, Cu, Zn, Fe, Ni, Co, Mo, Ti, Pt, or their compounds. Also suitable are, for example, S, Se, phosphates of transition metals such as V and Fe, and heteropolyacids such as molybdophosphoric acid.

Examples of specific catalysts are:

Sodium or sodium compounds (DE-A-37 19 055 and DE-A-38 11 509)

Aluminum oxide, alkali metal aluminate and/or alkaline earth metal aluminate (EP-A-04 05 348)

Silver oxide (JP-A 60/089 441, Derwent Report 85-15 68 91/26)

A catalyst comprising copper, zinc and sulfur (DE-A 25 25 174)

A catalyst comprising copper, zinc and selenium (US-A 4,054,609)

A catalyst comprising zinc and/or indium (EP-A 0 130 068)

Silver (US-A 2,953,602)

Silver, copper and silicon (US-A 2,939,883).

Preference is given to using sodium or sodium compounds.

The form in which such a catalyst, for example a sodium-containing catalyst, is used can vary widely:

Metallic, e.g. also as an alloy with at least one other alloy constituent, as compound or salt, where at least one nonmetallic element is chemically combined with Na (binary compounds and salts). If more than one element is present in chemically combined form in the compound, a binary, ternary or quaternary compound or a salt is present.

If sodium is used in metallic form, it can be used as solid, liquid or preferably as vapor.

Preferred alloys are those with other alkali metals and/or alkaline earth metals, for example Ba, Sr, Ca, Cs, Rb, K or, particularly preferably, Li and/or magnesium.

Furthermore, alloys with B, Al, Si and Sn can also be used. This also applies, in particular, to alloys which can comprise compounds such as sodium boride, $NaB_2$, sodium silicide, NaSi or NaSn.

Examples of suitable binary sodium compounds and salts are sodium carbides such as $Na_2C_2$, $NaC_8$, sodium halides such as NaF, sodium oxides such as $Na_2O$, sodium azide, sodium phosphide, sodium sulfide, sodium polysulfides, preferably also sodium hydrides such as NaH.

Examples of suitable ternary sodium compounds and salts are sodium borates such as borax, sodium phosphates or hydrogenphosphates, sodium phosphites, sodium (meta) silicates and aluminosilicates, e.g. water glass, $Na_3AlF_6$ (cryolite), sodium (hydrogen)sulfate, sodium sulfite, sodium nitrite, sodium nitrate, sodium amide, sodium acetylide NaCCH, sodium cyanide, sodium thiocyanate, the sodium salt of methyl thiol, sodium thiosulfate, but preferably NaOR, where R=H or an organic radical (=salts of organic acids, alkoxides, phenoxides, acetylacetonate, acetoacetic ester salt, salts of salicylic acid or salicylaldehyde), sodium carbonate and sodium hydrogencarbonate and mixtures thereof, for example soda, thermonatrite, trona, pirssonite, natrocalcite. The use of anhydrous, i.e. dried, salts is generally preferred.

Particular preference is given to NaOH, NaOOC—R (preferably formate, acetate, lactate, oxalate), NaOR=(R=is an organic radical having from 1 to 4 carbon atoms) and sodium carbides.

Very particular preference is given to NaOH, sodium formate, sodium methoxide, sodium acetate and sodium carbides such as $Na_2C_2$.

Suitable quaternary compounds are, for example, sodium-containing aluminosilicates which can be prepared synthetically or can also occur in a wide variety as natural minerals and rocks (e.g. sodium feldspar or albite and calcium-sodium feldspar or oligoclase). They can additionally be laden with Na by ion exchange.

Use can also advantageously be made of double salts of the alum type or thenardite, glauberite, astrakanite, glaserite, vanthoffite.

The sodium compounds and salts mentioned here can advantageously also be in the form of mixtures. In particular, it is also quite possible to use mixtures containing <50%, preferably <30%, of cations of other alkali metals and/or alkaline earth metals, e.g. Ba, Sr, Ca, Cs, Rb, K or preferably Li and/or magnesium. Industrially available, complex mixtures such as soda lime, ground basic slag and cements, e.g. Portland cement, if desired after enrichment with sodium by storage in sodium-containing solutions (NaCl, sea water) are particularly advantageous.

The abovementioned compounds used as catalysts give yields of over 70% at reaction temperatures of from 700 to 850° C. and low water concentrations of less than 5 mol% of $H_2O$ per mole of formaldehyde. Advantages of the lower reaction temperature are the lower energy and apparatus requirements for heating/cooling before/after the reaction, the low decomposition rate of the formaldehyde which is thermally unstable under the reaction conditions and the lower demands placed on the materials of construction.

The abovementioned substances will hereinafter be described as the primary catalyst.

The liberation of the catalytically active species from the primary catalyst is preferably carried out by thermal decomposition of the latter.

The primary catalyst can, for example, be introduced initially or afterwards, in each case continuously or discontinuously, as a solid, dissolved in a solvent, as a liquid or as a melt.

The further introduction of the primary catalyst as a solid, e.g. in powder form, particulate or compacted, is generally carried out by means of solids metering, e.g. using a reciprocating or rotary piston, a cell wheel lock, a screw or a vibrating chute.

If the primary catalyst is added in dissolved form, particularly suitable solvents are those having a chemical composition consisting only of the elements already present in the process (C,H,O). MeOH is particularly preferred as solvent. The addition is carried out, for example, via a nozzle which can be cooled in order to avoid evaporation of the solvent, crystallization or deposition of the solid primary catalyst in the nozzle.

The addition of the primary catalyst as a melt can be carried out, for example, via a nozzle. The melt can be vaporized or decomposed directly in the gas stream.

In all possible ways of subsequent introduction of the primary catalyst, this is advantageously carried out in a manner such that the material is in intimate contact with flowing gas. This can be achieved, for example, by applying the catalyst material according to the above-described processes to a suitable surface through or over which the gas flows. This can be the surface of a support material present as a fixed bed. Suitable materials are, for example, SiC, $SiO_2$ and $Al_2O_3$ in a suitable geometric form, e.g. as granules, pellets or spheres. The material is preferably arranged vertically in a fixed bed, preferably with metering in from above. The substance introduced deposits on the support material and the catalytically active species goes into the gas phase during the process.

Another possibility is arrangement of the primary catalyst in a fluidized bed through which the carrier gas stream is passed. The fluidized material comprises at least some of the supported or unsupported primary catalyst. The loss of active substance can be replaced by further introduction of fresh primary catalyst, exhausted material can be taken off if desired. In a continuous process, this can be realized, for example, by means of a circulating fluidized bed.

Subsequent introduction of the primary catalyst can also be carried out by alternating secondary catalyst generation in various vessels in which the primary catalyst can be arranged, for example as fixed bed or fluidized bed, in each case supported or unsupported.

The advantage of using a plurality of units for the discontinuous subsequent introduction of catalyst is that it is also possible to use those primary catalysts for which, e.g. owing to material properties such as melting point, viscosity or decomposition temperature, continuous introduction would be impossible or very costly.

In a preferred variant of the process of the invention, the generation of the secondary catalyst is carried out physically separately from the reaction zone in which the actual dehydrogenation takes place and at a temperature above the dehydrogenation temperature.

The temperature difference between the location of catalyst generation and the reaction zone is preferably at least 20° C., particularly preferably from 40 to 250° C.

On thermal treatment of the primary catalysts of the invention in the primary catalyst decomposition zone and on passing over a reducing or nonreducing gas such as molecular nitrogen at temperatures which may be different from the reaction temperature for the dehydrogenation and may be higher or lower, one or more catalytically active species which are able to catalyze the dehydrogenation of methanol are released or generated from the primary catalyst and/or generated on it (secondary catalyst). Such a fluid catalyst can be transported over considerable distances without suffering from an appreciable loss of effectiveness in the dehydrogenation. This separate setting of temperatures makes it possible, in particular, to lower the reaction temperature by matching to the respective conditions for catalyst liberation/varporization or generation of a catalytically active species (secondary catalyst) on the one hand and to the reaction on the other hand. This reduces the decomposition of the formaldehyde, which is unstable under the reaction conditions, as a result of secondary reactions and increases the yield.

Preferred temperatures for generating the secondary catalyst from the primary catalyst are from 300 to 1100° C.; particularly preferred temperatures are from 400 to 1000° C.

In addition, the residence times in the dehydrogenation reactor and vessels for adding primary catalyst or for generating the secondary catalyst can be set separately by dividing the carrier gas stream. This achieves targeted loading of the gas stream passed through the catalyst addition unit with the active species.

Preferred residence times for generating the secondary catalyst are from 0.01 to 60 sec, particularly preferably from 0.05 to 3 sec.

If the generation of the primary catalyst is carried out physically separately from the reaction zone, the temperatures in the reaction zone are generally from 200 to 1000° C., preferably from 300 to 980° C.

For the dehydrogenation of the methanol, the residence time in the reaction zone is preferably from 0.005 to 30 sec, particularly preferably from 0.01 to 15 sec, very particularly preferably from 0.05 to 3 sec.

Suitable reactors are well known to those skilled in the art. Essentially, it is possible to use reactor types and assemblies as are known from the literature for dehydrogenation reactions. Such apparatuses are described, for example, in Winnacker/Kuchler, Chemische Technologie, $4^{th}$ Edition, Chapter "Technik der Pyrolyse" Hanser Verlag, Munich 1981–86. Examples of suitable reactors are tube reactors; suitable reactor materials are, for example, ceramic materials such as a-alumina but also iron- and nickel-based alloys which are resistant to carbonization, heat and scale, e.g. Inconel 600® or Hasteloy ®.

If the reactor is heated by means of a combustion reaction, a suitable type of reactor is, for example, an externally fired tube reactor.

Preference is likewise given to heating the reactor by means of microwaves.

In a further preferred variant of the process of the invention, a carrier gas stream at a temperature above the dehydrogenation temperature is fed into the reactor.

The temperature difference between carrier gas stream and dehydrogenation temperature is preferably at least 20° C., particularly preferably from 40 to 250° C.

The superheated gas stream can be fed directly into the reaction zone or all or some of it can be brought into contact with the primary catalyst beforehand.

For the superheated gas stream, the preferred temperatures are from 600 to 1000° C., particularly preferably from 700 to 900° C. Preferred temperatures for the dehydrogenation of methanol are from 500 to 900° C.; particular preference is given to temperatures of from 600 to 800° C.

The carrier gas stream or streams can consist of a reducing or nonreducing gas, e.g. $H_2/CO$ mixtures or nitrogen, preferably the by-products of the dehydrogenation.

Such a process is subject matter of the German Patent Application 197 22 774.0 which is hereby expressly incorporated by reference into the present description.

The formaldehyde can be separated from the reaction mixture by methods known per se with which those skilled in the art are familiar, for example by condensation, polymerization or physical or chemical absorption or adsorption. An industrially proven method is the formation of hemiacetals from formaldehyde and an alcohol. The hemiacetals are subsequently dissociated thermally, giving very pure formaldehyde vapor. The alcohol used is usually cyclohexanol since its boiling point is sufficiently far above the decomposition temperature of the hemiacetal. The hemiacetals are usually dissociated in falling film or thin film evaporators at temperatures of from 100 to 160° C. (see, for example, U.S. Pat No. 2,848,500 of Aug. 19, 1958 "Preparation of Purified Formaldehyde" and U.S. Pat. No. 2,943,701 of Jul. 5, 1960 "Process for purification of gaseous formaldehyde", or JP-A 62/289 540). The formaldehyde vapors liberated in this dissociation still contain small amounts of impurities which are usually removed by countercurrent scraping with alcohol such as cyclohexanol hemiformal, by condensation or by controlled prepolymerization.

Particularly preferred methods of purifying the formaldehyde prepared according to the invention are described in the German Patent Applications 19 747 647.3 and 19 748 380.1.

A further method of separating formaldehyde from the reaction mixture is the formation of trioxane in a catalytic gas-phase process (see, for example, Appl. Catalysis A 1997, 150, 143→151 and EP-A 0 691 338). Trioxane can then, for example, be condensed out.

Further possible ways of utilizing the by-products of the reaction, in particular hydrogen, are, for example, the synthesis of methanol or the isolation of pure hydrogen which can, for example, be separated off by means of membranes.

The hydrogen obtained in this way is suitable, for example, for the synthesis of ammonia, in refinery processes for producing gasoline and petrochemical cracking products, for the synthesis of methanol, for hardening fats and for other hydrogenations, as reducing agent for producing W, Mo, Co and other metals, as reducing protective gas in metallurgical processes, for autogenous welding and cutting, as fuel gas in admixture with other gases (town gas, water gas), or in liquefied form as fuel in aerospace applications.

The formaldehyde prepared by the process of the invention is suitable for all known fields of application, for example corrosion protection, production of mirrors, electrochemical coatings, for disinfection and as a preservative, also as intermediate for preparing plastics, for example polyoxymethylenes, polyacetals, phenolic resins, melamines, amino-plastics, polyurethanes and casein plastics, 1,4-butanols, alcoholic formaldehyde solutions, methylal, trimethylolpropane, neopentyl glycol, pentaerythritol and trioxane, for producing dyes such as fuchsin, acridine, for producing fertilizers and for the treatment of seed.

The invention also relates to plastics such as polyoxymethylene and polyacetals, trioxane, dyes, fertilizers and seed produced in this way.

The invention further provides a process for preparing trioxane, which comprises 1. converting methanol into formaldehyde by dehydrogenation in a reactor in the presence of a catalyst at a temperature in the range from 300 to 1000° C., where a circulating gas stream comprising by-products of the dehydrogenation is passed through the reactor, and 2. if desired, purifying the formaldehyde prepared in this way and trimerizing it to give trioxane.

Details of the preparation of trioxane are well known to those skilled in the art. They are described, for example, in Kirk-Othmer, Encyclopedia of Chemical Technology, 2nd Edition, Volume 10, pp. 83, 89, New York Interscience 1963–1972.

The invention likewise provides a process for preparing polyoxymethylene, which comprises 1. converting methanol into formaldehyde by dehydrogenation in a reactor in the presence of a catalyst at a temperature in the range from 300 to 1000° C., where a circulating gas stream comprising by-products of the dehydrogenation is passed through the reactor, and 2. if desired, purifying the formaldehyde obtained in this way, 3. polymerizing the formaldehyde, 4. capping the end groups of the polymer prepared in this way and 5. if desired, homogenizing the polymer in the melt and/or providing it with suitable additives.

The preparation of polyoxymethylene from formaldehyde is well known to those skilled in the art. Details may be found, for example, in Ullmann's Encyclopedia of Industrial chemistry, Volume 21, 5th Edition, Weinheim 1992 and the literature cited therein.

The invention further provides a process for preparing polyoxymethylene copolymers, which comprises 1. converting methanol into formaldehyde by dehydrogenation in a reactor in the presence of a catalyst at a temperature in the range from 300 to 1000° C., where a circulating gas stream comprising by-products of the dehydrogenation is passed through the reactor, and 2. trimerizing the formaldehyde obtained in this way to give trioxane, 3. if desired, purifying the trioxane, 4. copolymerizing the trioxane with cyclic ethers or cyclic acetals, 5. if desired, removing unstable end groups and 6. if desired, homogenizing the polymer prepared in this way in the melt and/or admixing it with suitable additives.

The invention further provides a process for preparing polyoxymethylene copolymers, which comprises 1. converting methanol into formaldehyde by dehydrogenation in a reactor in the presence of a catalyst at a temperature in the range from 300 to 1000° C., where a circulating gas stream comprising by-products of the dehydrogenation is passed through the reactor, and
2. if desired, purifying the formaldehyde obtained in this way,
3. copolymerizing the formaldehyde with cyclic ethers or cyclic acetals,
4. if desired, removing unstable end groups and
5. if desired, homogenizing the polymer prepared in this way in the melt and/or admixing it with suitable additives.

The preparation of polyoxymethylene copolymers is well known to those skilled in the art. Details may be found, for example, in Ullmann's Encyclopedia of Industrial Chemistry, Volume 21, 5th Edition, Weinheim 1992 and the literature cited therein, and also in the Russian documents SU 436067, 740715 and SU 72-1755156, 720303.

The contents of the priority-establishing German Patent Applications 197 22 774.0, 197 27 519.2, 197 27 520.6 and 197 43 145.3 and also the abstract of the present application are expressly incorporated by reference into the present description.

The invention is illustrated by the examples without being limited thereby.

EXAMPLES

The conversion and yield are calculated as follows:

$$\text{conversion (in \%)} = \frac{\text{methanol reacted (mole)}}{\text{methanol fed in (mole)}} \cdot 100$$

$$\text{yield (in \%)} = \frac{\text{formaldehyde formed (mole)}}{\text{methanol fed in (mole)}} \cdot 100$$

Figure 2:
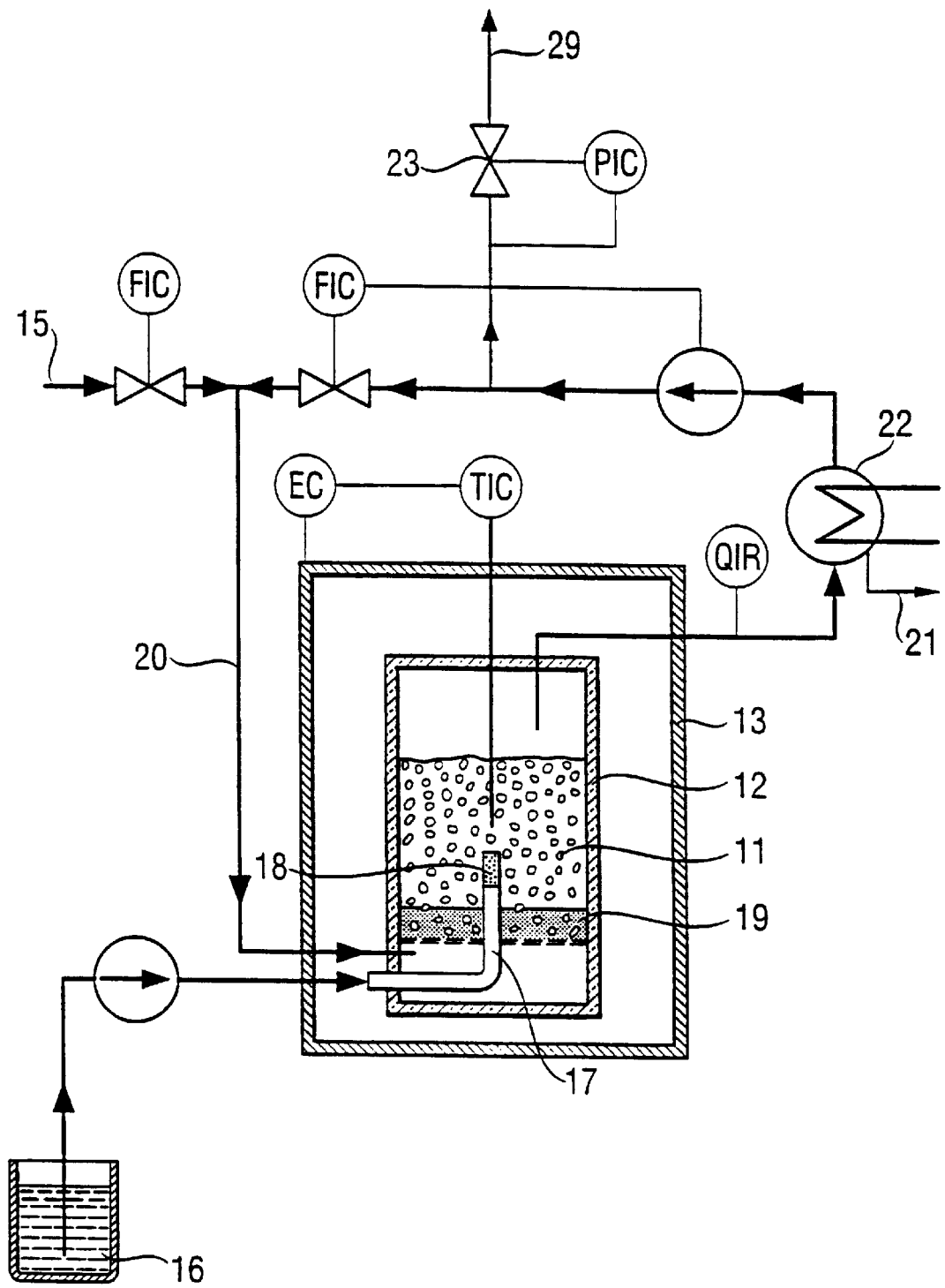
Figure 3:
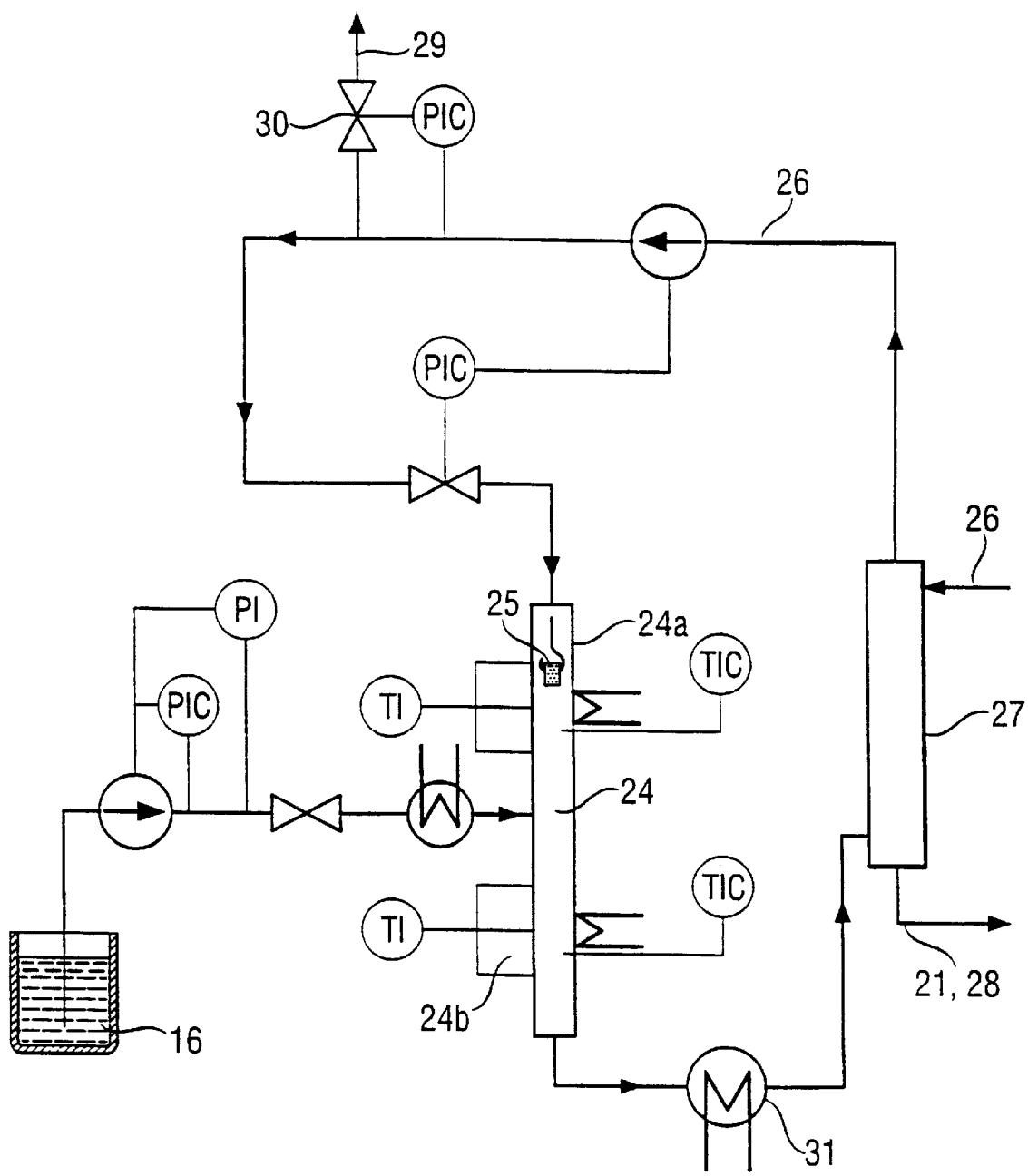

Experiments on the dehydrogenation of methanol which were carried out in a microwave-heated and in an electrically heated laboratory reactor are described below. FIG. 2 shows a schematic flow diagram of the configuration of the microwave-heated laboratory reactor, FIG. 3 shows that of the electrically heated laboratory reactor.

A. Reactor Heated by Microwaves

The actual reaction space is the interstitial space in a bed 11. The bed 11 comprises SiC spheres having a diameter of a few millimetres and is located in a quartz reactor 12. For heating, the reactor 12 is installed in a microwave heating chamber 13 where heat is liberated in the SiC spheres as a result of irradiation. This method of reactor heating makes it possible to achieve a significantly more homogeneous temperature distribution than, for example, in externally heated tubes. The temperature is measured in the bed and is set by regulating (TIC) the power of the radiation.

A carrier gas 15 (preferably nitrogen) flows through the bed 11 from the bottom upward. Methanol 16 is introduced through a vertical tube 17 extending to about half the height of the bed 11 and there goes through a frit 18 into the bed 11 where it mixes with the carrier gas 15. Primary catalysts 19 in tho form of grains are introduced into the lower quarter of the bed 11. Apart from the methanol 16, either the carrier gas 15 is fed into the reactor 12 or the reaction products after separating off the formaldehyde 21 in a cold trap 22 are recirculated to the reactor 12 as circulating gas 20. Excess reaction gas and/or carrier gas 15 can be discharged under pressure control via a valve 23.

The total volume flow is from 20 l/h to 500 l/h, the residence time within the bed varies from 0.02 to 1 s and the proportion of methanol is from 5 to 50 mol%. As solid, various alkali metal compounds are used. The reaction product is analyzed by means of a gas chromatograph.

TABLE 1

Conversion and formaldehyde yield in the pyrolysis of methanol (residence time at the reaction temperature about 0.2 s, inlet concentration of methanol about 10 mol %, amount of catalyst corresponding to about 0.5 g of alkali metal)

| Example/ comparative example | Solid (catalyst) | Temperature in the bed | Conversion of methanol | Yield in $N_2$ | Yield in circulating gas |
|---|---|---|---|---|---|
| Ex. 1 | none | approx. 910° C. | 60% | | 12% |
| CE 1 | none | approx. 920° C. | 70% | 11% | |
| Ex. 2 | $Na_2CO_3$ | approx. 880° C. | 93% | | 67% |
| CE 2 | $Na_2CO_3$ | approx. 880° C. | 92% | 63% | |
| Ex. 3 | NaOH | — | 80% | | 54% |
| Ex. 4 | $NaCHO_2$ | approx. 790° C. | 91% | | 65% |
| CE 3 | $NaCHO_2$ | approx. 820° C. | 83% | 52% | |
| Ex. 5 | $NaC_2H_3O_2$ | approx. 780° C. | 92% | | 63% |
| CE 4 | $NaC_2H_3O_2$ | approx. 760° C. | 84% | 55% | |
| Ex. 6 | $LiOCH_3$ | approx. 780° C. | 91% | | 39% |
| CE 5 | $LiOCH_3$ | approx. 795° C. | 95% | 32% | |
| Ex. 7 | $Cs_2CO_3$ | approx. 865° C. | 90% | | 26% |
| CE 6 | $Cs_2CO_3$ | approx. 900° C. | 90% | 22% | |
| Ex. 8 | $KOCH_3$ | approx. 845° C. | 88% | | 27% |
| CE 7 | $KOCH_3$ | approx. 840° C. | 88% | 20% | |
| Ex. 9 | $Na_2C_2$ | approx. 765° C. | 77% | | 58% |
| Ex. 10 | $Na_2C_2$ | approx. 775° C. | 89% | | 58% |
| CE 8 | $Na_2C_2$ | approx. 805° C. | 80% | 53% | |
| Ex. 11 | $Na_2(COO)_2$ | approx. 785° C. | 87% | | 51% |
| Ex. 12 | $NaOCH_3$ | approx. 760° C. | 91% | | 70% |
| CE 9 | $NaOCH_3$ | approx. 760° C. | 89% | 62% | |

TABLE 2

Conversion and formaldehyde yield in the pyrolysis of methanol (residence time at the reaction temperature about 0.1 s, inlet concentration of methanol about 10 mol %, amount of catalyst corresponding to about 0.5 g of alkali metal)

| Example/ comparative example | Solid (catalyst) | Temperature in the bed | Conversion of methanol | Yield in $N_2$ | Yield in circulating gas |
|---|---|---|---|---|---|
| CE10 | $NaC_2H_3O_2$ | approx. 785° C. | 92% | | 76% |
| Ex. 13 | $NaC_2H_{3O2}$ | approx. 805° C. | 92% | 69% | |
| Ex. 14 | $Na_2C_2$ | approx. 780° C. | 89% | | 67% |
| Ex. 15 | $Na_2C_2$ | approx. 765° C. | 83% | | 68% |
| Ex. 16 | $Na_2(COO)_2$ | approx. 775° C. | 94% | | 68% |
| CE 11 | $Na_2(COO)_2$ | approx. 765° C. | 81% | 62% | |

B. Electrically Heated Reactor

The dehydrogenation of the methanol 16 is carried out in a tube reactor 24 heated by means of electrical laboratory furnaces (see FIG. 3). The catalyst 25 (0.1–5 g) is placed in a tube in the first furnace 24a (700–1000° C.) and circulating gas 26 is passed over it. Downstream of this, the preheated methanol 16 (20–500 g/h, 400–800° C.) is fed in. This is followed by the actual reaction zone 24b (tube; length of 20–50 cm, internal diameter 7–20 mm) in a second furnace (700–1000° C.). Immediately after the reactor, the reaction products are cooled to about 150° C. In a column 27, the reaction products are scrubbed with alcohol 28 (e.g. cyclohexanol at 20–80° C.) in order to remove 21, 28 the formaldehyde 21. After the scrub, the excess 29 of the gaseous products is discharged under pressure control (PIC) by means of a valve 30 and the remainder is recirculated as circulating gas 26 (100–2000 l/h) and is preheated in the first furnace 24a.

The use of
80 g/h of methanol
400 l/h of circulating gas
1 g of sodium methoxide as catalyst
gives 54 g/h of formaldehyde.

What is claimed is:

1. A process for preparing formaldehyde from methanol by dehydrogenation in a reactor in the presence of a catalyst at a temperature in the range from 300 to 1000° C., wherein a circulating gas stream comprising by-products of the dehydrogenation is passed through the reactor.

2. The process as claimed in claim 1, wherein the circulating gas stream consists essentially of $H_2$ and CO.

3. The process as claimed in claim 2, wherein the molar ratio $H_2$/CO in the circulating gas is 3.

4. The process as claimed in claim 1, wherein the reactor is an externally fired tube reactor.

5. The process as claimed in claim 1, wherein the reactor is heated by means of microwaves.

6. The process as claimed in claim 1, wherein a further part of the by-products of the dehydrogenation is used as fuel for heating the reactor.

7. The process as claimed in claim 1, wherein the catalyst used is sodium or a sodium compound which contains, apart from Na, only elements selected from the group consisting of C, H and O.

8. An apparatus for carrying out a process as claimed claim 1, comprising a heat exchanger for preheating the starting materials, a reactor for carrying out the dehydrogenation, a heat exchanger for cooling the product mixture, a separation vessel for separating off the formaldehyde and means for recirculating at least part of the by-products of the dehydrogenation (circulating gas) to the reactor.

9. An apparatus as claimed in claim 8 which comprises means for discharging a further part of the by-products of the dehydrogenation and feeding this part to an apparatus for heating the reaction in which latter apparatus it serves as fuel.

10. The process as claimed in claim 1, wherein part of hydrogen obtained as by-product is separated off.

11. A process for preparing trioxane, which comprises
converting methanol into formaldehyde by dehydrogenation in a reactor in the presence of a catalyst at a temperature in the range from 300 to 1000° C., where a circulating gas stream comprising by-products of the dehydrogenation is passed through the reactor, and
trimerizing the formaldehyde to give trioxane.

12. A process for preparing polyoxymethylene, which comprises
converting methanol into formaldehyde by dehydrogenation in a reactor in the presence of a catalyst at a temperature in the range from 300 to 1000° C., where a circulating gas stream comprising by-products of the dehydrogenation is passed through the reactor, and
if desired, purifying the formaldehyde,
polymerizing the formaldehyde,
capping the end groups of the polymer and
if desired, homogenizing the polymer in the melt and/or providing it with additives.

13. A process for preparing polyoxymethylene copolymers, which comprises
converting methanol into formaldehyde by dehydrogenation in a reactor in the presence of a catalyst at a temperature in the range from 300 to 1000° C., where a circulating gas stream comprising by-products of the dehydrogenation is passed through the reactor, and
trimerizing the formaldehyde to give trioxane,
if desired, purifying the trioxane,
copolymerizing the trioxane with cyclic ethers or cyclic acetals,
if desired, removing unstable end groups and
if desired, homogenizing the polymer in the melt and/or admixing it with additives.

14. A process for preparing polyoxymethylene copolymers, which comprises,
converting methanol into formaldehyde by dehydrogenation in a reactor in the presence of a catalyst at a temperature in the range from 300 to 1000° C., where a circulating gas stream comprising by-products of the dehydrogenation is passed through the reactor, and if desired, purifying the formaldehyde, copolymerizing the formaldehyde with cyclic ethers or cyclic acetals, if desired, removing unstable end groups and if desired, homogenizing the polymer in the melt and/or admixing it with additives.

* * * * *

UNITED STATES PATENT AND TRADEMARK OFFICE
CERTIFICATE OF CORRECTION

PATENT NO.       : 6,362,305 B1
APPLICATION NO.  : 09/445083
DATED            : March 26, 2002
INVENTOR(S)      : Elke Schweers et al.

It is certified that error appears in the above-identified patent and that said Letters Patent is hereby corrected as shown below:

column 12, line 61 after "polymer" insert - - prepared in this way - -.

Signed and Sealed this

Twenty-second Day of August, 2006

JON W. DUDAS
*Director of the United States Patent and Trademark Office*